United States Patent [19]

List

[11] Patent Number: 5,695,778
[45] Date of Patent: Dec. 9, 1997

[54] THERAPEUTIC SYSTEM FOR THE TREATMENT OF PSORIASIS

[75] Inventor: Harald List, Neuwied, Germany

[73] Assignee: LTS Lohmann Therapie-Systeme GmbH, Neuwied, Germany

[21] Appl. No.: 601,064

[22] PCT Filed: Aug. 10, 1994

[86] PCT No.: PCT/EP94/02650

§ 371 Date: Jun. 27, 1996

§ 102(e) Date: Jun. 27, 1996

[87] PCT Pub. No.: WO95/05829

PCT Pub. Date: Mar. 2, 1995

[30] Foreign Application Priority Data

Aug. 21, 1993 [DE] Germany .......................... 43 28 217.2

[51] Int. Cl.⁶ ................................................. A61F 13/00
[52] U.S. Cl. ........................... 424/448; 424/449; 514/863
[58] Field of Search ..................... 424/448, 449; 514/863

[56] References Cited

U.S. PATENT DOCUMENTS

Re. 34,692  8/1994  Becher ................................. 424/448
5,532,228   7/1996  Neef .................................... 514/167

FOREIGN PATENT DOCUMENTS 0 227 826   7/1987  European Pat. Off. .
2 135 533   2/1973  Germany .
3 315 272   3/1986  Germany .

OTHER PUBLICATIONS

Heilmann, "Therapeutische Systeme", Ferdinand Enke Verlag, Stuttgart, Germany, 1984, p. 27.

*Primary Examiner*—D. Gabrielle Phelan
*Attorney, Agent, or Firm*—Wenderoth, Lind & Ponack

[57] ABSTRACT

A therapeutic system for topically administering active substances for the treatment of skin diseases involving severe cell proliferation is characterized in that the active substance is a pharmaceutically acceptable derivative of vitamin $D_3$, with the exception of such derivates as serve to regulate the calcium metabolism.

11 Claims, No Drawings

THERAPEUTIC SYSTEM FOR THE TREATMENT OF PSORIASIS

The present invention relates to a therapeutic system for administering active substances belonging to the group of vitamin $D_3$ derivatives which are suitable for use in the treatment of skin diseases characterized by abnormal cell proliferation and/or disturbed cell differentiation.

A great number of people—in Germany alone there are presumed to be 2 millions concerned—suffer from psoriasis of different degrees of severity. This makes psoriasis one of the most frequent skin diseases. The cause for this skin disease is a genetic change which influences the immune defence of the organism. For this reason, no possibility of a cure has been found to this day. However, there are methods of treatment available which can give considerable relief.

These are, first of all, external applications involving the application of active substances that reduce the accelerated cellular proliferation which is accompanied by scale formation, e.g. preparations of coal tar, salicylic acid, dithranol, cortisone, fumaric acid derivatives. A further therapeutic method is that of photochemotherapy. Occlusive dressings also contribute to an improvement. In addition, in severe cases of psoriasis, internally active preparations such as glucocorticoids, vitamin A derivatives, cytostatic agents (methotrexate) or immunotherapeutics (cyclosporin A) are being used.

All these methods, which have been dealt with in numerous publications, have disadvantages and side effects such as 1. nephrotoxicity
2. embryotoxicity
3. gastrointestinal side effects
4. rebound effects.

Some agents which are to be applied locally require an additional covering in order to prevent clothing from being soiled.

It has been known for some years that the naturally occurring vitamin $D_3$ is also capable of influencing psoriasis: in cell cultures vitamin $D_3$ inhibited cell proliferation and induced a well-differentiated formation of cells.

Where a dosage as required for achieving a significant effect was used, however, it turned out that vitamin $D_3$ interfered considerably with the calcium metabolism, both in oral and in cutaneous application. Consequently, a therapeutic use in the treatment of psoriasis was not possible. For this reason vitamin $D_3$ derivates were synthesized with the intent of preventing or at least considerably reducing the side effects caused by vitamin $D_3$, i.e. hypercalcemia, bone absorption and hypercalciuria.

Vitamin $D_3$ derivatives which serve to regulate the calcium metabolism, such as calcitriol, can therefore not be used for the purposes of the present invention. The synthesis of new vitamin $D_3$ analogues has been published in EP 0 227 826 and WO 89/10 351. The substance calcipotriol described therein is now available for therapeutic use.

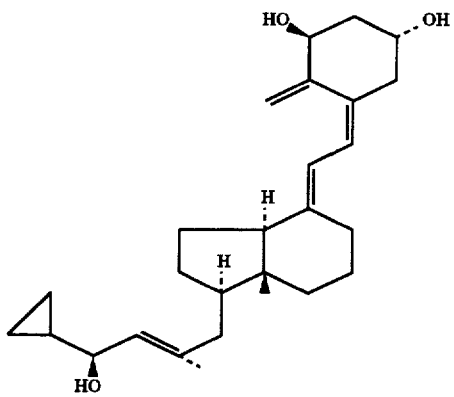

Graphic Formula of Calcipotriol

The use of active substances in therapeutic systems has not been described in these patents.

Of the plurality of derivatives described the synthetic 1,24-dihydroxy derivative of vitamin $D_3$ (INN calcipotriol), in particular, proves to be just as effective in the cell culture in inducing differentiation and inhibiting proliferation in keratinocyte cultures as the vitamin $D_3$ itself, its negative influence on the calcium metabolism, however, only amounting to a hundredth of that of vitamin $D_3$.

The therapeutic efficacy of calcipotriol-containing products in comparison to the standard methods of treatment has been proved. The active substance is to be used twice daily and has turned out to be well tolerated, with the exception of occasional burning sensations and itching. However, the dosis and thus the area which can be treated is limited due to the fact that with higher dosage an influence on the calcium metabolism is still possible: Thus a maximum of 15 grams per day or a maximum of 100 grams per week of an ointment preparation containing 50 micrograms of calcipotriol in 1 gramme of ointment is not to be exceeded.

It is the object of the present invention to provide an administration form which increases the efficacy of the active substance, i.e. improves the dosis/effect relation, further reduces side effects or avoids them altogether, and enables an application method which is acceptable to the user.

This object is achieved in accordance with the invention in that for the application of calcipotriol or other pharmaceutically acceptable vitamin $D_3$ derivatives which do not serve to regulate the calcium metabolism, a therapeutic system is employed. A therapeutic system is a drug-containing device or administration form which releases one or more drugs at a predetermined rate, continuously, over a defined period of time, to a defined application site (quoted according to HEILMANN, "Therapeutische Systeme", Ferdinand-Enke-Verlag, Stuttgart 1984).

As a matter of course, the use of prodrugs is also possible.

The use of therapeutic systems in the administration of active substances belonging to the group of vitamin $D_3$ derivatives, means that application intervals, especially in local application, can be prolonged, that the controlled active substance liberation prevents absorption peaks with subsequent systemic effect, that the treatment of larger areas of skin is made possible, and that the duration of treatment, which has so far been limited, can be prolonged, even with interruptions—a very important factor in view of the life-long necessity for treatment.

Moreover, such a therapeutic system at the same time provides a useful covering of the treated skin areas, which covering may remain on the skin for up to several days depending on the composition thereof. The therapeutic system has the positive effect of occlusion, which is known from the literature, and the patients' hygienic needs can be solved satisfactorily. Application is effected after cutting the systems to the shape and size of the skin areas concerned.

Preferred therapeutic systems within the scope of the invention are, for example, those in plaster form; they may, in principle, be present as:
1. membrane-controlled systems
2. matrix-controlled systems.

An example for plasters with membrane control is DE-A 21 35 533. These plasters, in principle, consist of a backing layer, forming one of the surfaces, a layer of adhesive which is permeable to the active substance and forms the other surface, and finally a reservoir comprising the active substance between the two layers forming the surfaces.

As an alternative, the active substance may also be contained in a plurality of microcapsules which are distributed within the permeable layer of adhesive.

In any case, the active substance is continuously delivered from the reservoir or the microcapsules through a membrane into the active substance-permeable layer of adhesive, which is in contact with the patient's skin. In the case of microcapsules, the capsule material may also serve as a membrane.

A plaster having matrix diffusion control is described, for example, in DE-PS 33 15 272. It consists of an impermeable backing layer, a polymer matrix reservoir attached thereto which has a special structure and contains the active substance in a concentration exceeding the saturation concentration, a layer of adhesive connected to the reservoir and being permeable to the active substance, and a protective layer covering the layer of adhesive and being removable for use. Where the reservoir matrix is itself pressure-sensitive adhesive, the additional layer of adhesive can be dispensed with.

The dosage of calcipotriol or one of the other pharmacologically acceptable vitamin $D_3$ derivatives must be selected such that release rates are achieved the therapeutic efficacy of which equals that of ointment application. It must be taken into account in this connection that the therapeutic system can also remain on the skin for several days, if appropriate.

Advantageously, these systems release between 0.05 and 5.0 micrograms of the vitamin $D_3$ derivative per $cm^2$ and 24 h.

The therapeuctic systems described are used for the preparation of ready-for-use medicaments. This requires the establishing of parameters such as selection of active substance, dosis, control of release and release rate, composition of the reservoir and, as the case may be, addition of auxiliary substances. Thus, adding permeation enhancers, e.g. DMSO or AZON© can be useful for increasing the absorption in lower skin layers. For the same reason, a further principle may also be considered for improving the permeation of active substances, namely the use of electric current (iontophoresis).

The active substances may be introduced into a therapeutic system in different form; they may also be present in microencapsulated form. Finally, it may be useful to combine a vitamin $D_3$ analogue or vitamin $D_3$ derivate with other active substances—with the aim of increasing efficacy, but also with the aim of reducing the individual doses if required. Combinations are possible, for example, with cortisone, alpha-tocopherol, acetylsalicylic acid and/or fumaric acid. Advantageously, the therapeutic system comprises an active substance-containing reservoir on the basis of a gel layer or colloid layer, for example in the form of a polyacrylate hydrogel or a hydrocolloid of gelatin, pectin or carboxymethyl cellulose.

Summarizing, the following advantages can be achieved with the above-described therapeutic system which contains as active substance a pharmaceutically acceptable derivative or analogue of vitamin $D_3$ in the treatment of skin deseases involving abnormal cell proliferation and/or disturbed cell differentiation:

- controlled, constant active substance release along with the avoidance of systemic availability,
- improved dosis/effect-relation, avoidance of the limitations with regard to the duration of treatment and the extent of the skin areas treated which apply to common, topic application
- optimized treatment also with regard to therapeutic systems having a protective function at the same time,
- improved acceptance with the user.

I claim:

1. A therapeutic system for the administration of active substances in the treatment of skin diseases involving abnormal cell proliferation, said system being in the form of a plaster and comprising a backing layer, an active substance reservoir connected thereto and made up of a polymer matrix, and, where no other control mechanisms are present, a membrane controlling the active substance release, pressure sensitive adhesive means for affixing the system to the skin and, optionally, a protective layer which is removable prior to application, and said system containing calcipotriol of the formula

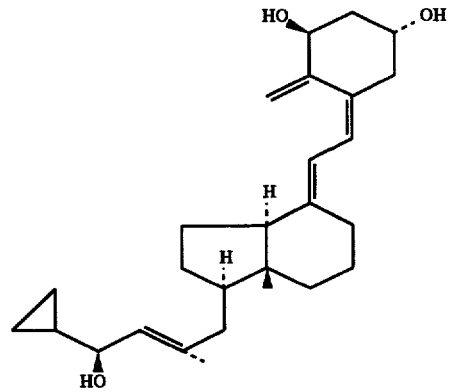

as active substance.

2. A therapeutic system according to claim 1, wherein the active substance is present as a prodrug.

3. A therapeutic system according to claim 1, wherein the system releases between 0.05 to 5.0 micrograms of the calcipotriol per $cm^2$ per 24 hours.

4. A therapeutic system according to claim 1 comprising a highly flexible, water vapour-permeable polymer film or sheet as backing layer.

5. A therapeutic system according to claim 4, wherein the polymer is a polyurethane.

6. A therapeutic system according to claim 1, wherein the active substance reservoir is formed with the aid of a gel layer or colloid layer.

7. A therapeutic system according to claim 1, wherein the diffusion of the active substance from the reservoir, or the permeation of the active substance into the skin is influenced by the addition of suitable substances.

8. A therapeutic system according to claim 1, wherein a combination of the calcipotriol with other active substance is used.

9. A therapeutic system according to claim 8, wherein the other active substance is at least one member selected from the group consisting of cortisone, alpha-tocopherol, acetylsalicylic acid and fumaric acid.

10. A process for the production of a therapeutic system according to claim 1, wherein calcipotriol is introduced into the administration system in solid form, in solution or in dispersion, optionally with the addition of auxiliary agents.

11. A method for the treatment of skin diseases involving abnormal cell proliferation which comprises applying to the skin of a patient suffering from such disease a therapeutic system as defined in claim 1.

* * * * *